US012565471B2

(12) United States Patent

Okamoto et al.

(10) Patent No.: US 12,565,471 B2

(45) Date of Patent: Mar. 3, 2026

(54) ISOBUTYRATE ESTER COMPOUND HAVING CARBONATE GROUP AT ALPHA-POSITION, AND FRAGRANCE COMPOSITION

(71) Applicant: MITSUBISHI GAS CHEMICAL COMPANY, INC., Chiyoda-ku (JP)

(72) Inventors: Atsushi Okamoto, Niigata (JP); Kyoko Hiraoka, Niigata (JP); Wataru Hamajima, Niigata (JP); Umi Yokobori, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 848 days.

(21) Appl. No.: 17/787,543

(22) PCT Filed: Dec. 22, 2020

(86) PCT No.: PCT/JP2020/047848

§ 371 (c)(1),
(2) Date: Jun. 20, 2022

(87) PCT Pub. No.: WO2021/132211

PCT Pub. Date: Jul. 1, 2021

(65) Prior Publication Data

US 2022/0402857 A1 Dec. 22, 2022

(30) Foreign Application Priority Data

Dec. 24, 2019 (JP) ................................ 2019-233331

(51) Int. Cl.
*C07C 69/96* (2006.01)
*C11B 9/00* (2006.01)

(52) U.S. Cl.
CPC ............ *C07C 69/96* (2013.01); *C11B 9/0019* (2013.01)

(58) Field of Classification Search
CPC .............................. C07C 69/96; C11B 9/0019
See application file for complete search history.

(56) References Cited

U.S. PATENT DOCUMENTS

| | | | |
|---|---|---|---|
| 3,368,943 | A | 2/1968 | Gilbert et al. |
| 4,668,433 | A | 5/1987 | Ochsner |
| 2014/0087990 | A1 | 3/2014 | Kitamura |

FOREIGN PATENT DOCUMENTS

| | | | |
|---|---|---|---|
| CN | 103415500 | A | 11/2013 |
| EP | 1 016 699 | A1 | 7/2000 |
| JP | 61-93141 | A | 5/1986 |
| JP | 2009-235002 | A | 10/2009 |
| JP | 2015-18667 | A | 1/2015 |
| WO | WO 2020/004465 | A1 | 1/2020 |
| WO | WO 2020/004466 | A1 | 1/2020 |
| WO | WO 2020/004467 | A1 | 1/2020 |
| WO | WO 2020/004468 | A1 | 1/2020 |
| WO | WO 2020/175241 | A1 | 9/2020 |

OTHER PUBLICATIONS

STN Registry Database entry for CAS RN 500790-25-0, entered STN Mar. 27, 2003; Accessed Mar. 29, 2025.*

STN Registry Database entry for CAS RN 132854-30-9, entered STN Mar. 29, 1991; Accessed Jul. 12, 2025.*

STN Registry Entry for CAS RN 112047-58-2; Entered STN Dec. 25, 1987; Accessed Oct. 17, 2025.*

International Search Report issued on Mar. 16, 2021 in PCT/JP2020/047848 filed on Dec. 22, 2020, 3 pages.

Shapiro et al., "Aminoalkylamides and Oxazolidinediones", Journal of the American Chemical Society, 1959, vol. 81, pp. 3083-3088.

Rehberg et al., "Mixed Esters of Lactic and Carbonic Acids. Reaction of Chloroformates With Esters of Lactic Acid", Journal of Organic Chemistry, 1948, vol. 13, pp. 254-264.

Cipollone et al., "Reaction of Ethyl Azidoformate with Ketene Silyl Acetals", Journal of Organic Chemistry, 1987, vol. 52, pp. 2584-2586.

Koryo, "Kagaku to Shohin Chisiki, zoho sinban (Synthetic fragrance: chemistry and product knowledge, new enlarged edition)", The Chemical Daily Co. Ltd., 2016, pp. 580-582.

* cited by examiner

*Primary Examiner* — Alicia L Otton

(74) *Attorney, Agent, or Firm* — Oblon, McClelland, Maier & Neustadt, L.L.P.

(57) ABSTRACT

A fragrance composition containing a compound represented by Formula (1) as an active ingredient:

(1)

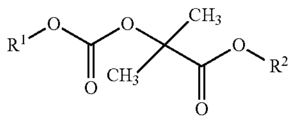

where in Formula (1), $R^1$ represents a linear, branched, or cyclic alkyl group having from 1 to 4 carbon(s); and $R^2$ represents a linear, branched, or cyclic alkyl group having from 1 to 6 carbon(s).

6 Claims, No Drawings

ISOBUTYRATE ESTER COMPOUND HAVING CARBONATE GROUP AT ALPHA-POSITION, AND FRAGRANCE COMPOSITION

CROSS-REFERENCE TO RELATED APPLICATIONS

The present application is a 35 U.S.C. § 371 national stage application of International patent application PCT/JP2020/047848, filed Dec. 22, 2020, which is based on and claims the benefit of priority to Japanese Application No. 2019-233331, filed Dec. 24, 2019. The entire contents of these applications are incorporated herein by reference.

TECHNICAL FIELD

The present invention relates to an isobutyric acid ester compound having a carbonate group at the α-position and a fragrance composition.

BACKGROUND ART

Some isobutyric acid esters are known to be compounds useful as fragrances. For example, Non-Patent Literature 1 describes that various isobutyric acid esters are mainly used as flavors, and all the isobutyric acid esters are flavor materials having a fruit scent; specifically, methyl isobutyrate gives a sweet apricot-like scent, propyl isobutyrate gives a strong pineapple-like scent, butyl isobutyrate gives a fresh apple- and banana-like scent, and isoamyl isobutyrate gives a sweet apricot- and pineapple-like scent.

Additionally, Patent Document 1 discloses that, as an isobutyric acid ester having a bond with oxygen at α-position, a straight-chain or branched alkyl ester of α-alkoxyisobutyric acid, the alkyl ester having 4 to 12 carbon atoms, is useful as a fragrance, and n-hexyl α-ethoxyisobutyrate has a lavender-like aroma.

On the other hand, isobutyric acid esters having a carbonate group at the α-position also include known substances; for example, Non-Patent Literature 2 discloses that ethyl α-(n-pentyloxycarbonyl)oxyisobutyrate and ethyl α-(n-butoxycarbonyl)oxyisobutyrate are useful as plasticizers for cellulose resins and vinyl resins.

Non-Patent Literature 3 discloses that ethyl α-(ethoxycarbonyl)oxyisobutyrate can be synthesized by reacting ethyl α-hydroxyisobutyrate and diethyl carbonate in the presence of a sodium ethoxide catalyst.

Non-Patent Literature 4 discloses that methyl α-(ethoxycarbonyl)oxyisobutyrate is produced by hydrolysis reaction of the corresponding trimethylsilyl carboimide compound.

CITATION LIST

Patent Documents

Patent Document 1: U.S. Pat. No. 3,368,943

Non-Patent Literatures

Non-Patent Literature 1: "Gousei Koryo: Kagaku to Shohin Chisiki, zoho sinban (Synthetic fragrance: chemistry and product knowledge, new enlarged edition)", The Chemical Daily Co. Ltd., 2016, p. 580 to 582

Non-Patent Literature 2: Journal of Organic Chemistry, 1948, Vol. 13, p. 254-264

Non-Patent Literature 3: Journal of the American Chemical Society, 1959, Vol. 81, p. 3083-3088

Non-Patent Literature 4: Journal of Organic Chemistry, 1987, vol. 52 (12), p. 2584-2586

SUMMARY OF INVENTION

Technical Problem

An object to be solved by the present invention is to provide an isobutyric acid ester compound having a carbonate group at the α-position useful as a fragrance and fragrance ingredient. Yet another object to be solved by the present invention is to provide a fragrance composition containing the compound as an active ingredient.

Solution to Problem

The present inventors have synthesized various compounds and diligently studied the aromas of these compounds and found that a specific ester compound of an isobutyric acid ester compound having a carbonate group at the α-position is useful as a fragrance and fragrance ingredient.

That is, the present invention is as follows.

<1> A fragrance composition containing a compound represented by Formula (1) as an active ingredient:

[Chem. 1]

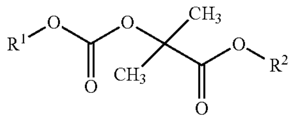

(1)

where in Formula (1), $R^1$ represents a linear, branched, or cyclic alkyl group having from 1 to 4 carbon(s); and $R^2$ represents a linear, branched, or cyclic alkyl group having from 1 to 6 carbon(s).

<2> The fragrance composition according to <1>, wherein in Formula (1), $R^1$ is a methyl group or an ethyl group.

<3> The fragrance composition according to <1> or <2>, wherein in Formula (1), $R^2$ is an isopropyl group, a sec-butyl group, or an isobutyl group.

<4> A compound represented by Formula (2):

[Chem. 2]

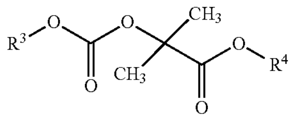

(2)

where in Formula (2), $R^3$ represents a linear, branched, or cyclic alkyl group having from 1 to 4 carbon(s); and $R^4$ represents a linear, branched, or cyclic alkyl group having from 1 to 6 carbon(s), with the proviso that the following are excluded: a compound where $R^3$ is an ethyl group and $R^4$ is a methyl group; a compound where $R^3$ is an ethyl group and $R^4$ is an ethyl group; and a compound where $R^3$ is a n-butyl group and $R^4$ is an ethyl group.

<5> The compound according to <4>, wherein in Formula (2), $R^3$ is a methyl group or an ethyl group.

<6> The compound according to <4> or <5>, wherein in Formula (2), $R^4$ is an isopropyl group, a sec-butyl group, or an isobutyl group.

Advantageous Effects of Invention

The present invention can provide the isobutyric acid ester compound useful as a fragrance and a fragrance ingredient, the isobutyric acid ester compound having a carbonate group at the α-position. Further, the present invention can provide the fragrance composition containing the isobutyric acid ester compound having a carbonate group at the α-position as an active ingredient.

DESCRIPTION OF EMBODIMENTS

[Fragrance Composition and Use]

A fragrance composition of the present invention contains a compound represented by Formula (1) below as an active ingredient. Although some of isobutyric acid ester compounds having a carbonate group at the α-positions have been known, there has been no description of the scent peculiar to the isobutyric acid esters having a carbonate group at the α-position.

Hereinafter, the present invention will be described in detail.

<Compound Represented by Formula (1)>

A compound used in the fragrance composition of the present invention (hereinafter also referred to as the "isobutyric acid ester having a carbonate group at the α-position") is represented by Formula (1) below:

[Chem. 3]

(1)

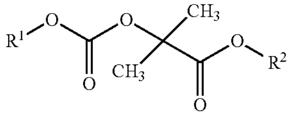

where in Formula (1), $R^1$ represents a linear, branched, or cyclic alkyl group having from 1 to 4 carbon(s); and $R^2$ represents a linear, branched, or cyclic alkyl group having from 1 to 6 carbon(s).

Examples of $R^1$ in Formula (1) specifically include a methyl group, an ethyl group, a n-propyl group, an isopropyl group, a n-butyl group, an isobutyl group (2-methylpropyl group), a sec-butyl group (1-methylpropyl group), a tert-butyl group, a cyclopropyl group, and a cyclobutyl group. $R^1$ is preferably a methyl group, an ethyl group, a n-propyl group, an isopropyl group, a n-butyl group, or an isobutyl group (2-methylpropyl group), and more preferably a methyl group or an ethyl group.

Examples of $R^2$ in Formula (1) specifically include a methyl group, an ethyl group, a n-propyl group, an isopropyl group, a n-butyl group, an isobutyl group (2-methylpropyl group), a sec-butyl group (1-methylpropyl group), a tert-butyl group, a n-pentyl group, a 1-methylbutyl group (2-pentyl group), a 2-methylbutyl group, a 3-methylbutyl group, a neopentyl group (2,2-dimethylpropyl group), a 2-methylbutan-2-yl group, a 1-ethylpropyl group (3-pentyl group), a 3-methylbutan-2-yl group, a n-hexyl group, a 1-methylpentyl group (2-hexyl group), a 2-methylpentyl group, a 3-methylpentyl group, a 4-methylpentyl group, a 2-methylpentan-2-yl group, a 2,2-dimethylbutyl group, a 3,3-dimethylbutyl group, a 3-methylpentan-2-yl group, a 2,3-dimethylbutyl group, a 4-methylpentan-2-yl group, a 3-hexyl group, a 2-ethylbutyl group, a 2,3-dimethylbutan-2-yl group, a 3,3-dimethylbutan-2-yl group, a 4-methylpentan-3-yl group, a cyclopropyl group, a cyclobutyl group, a cyclopentyl group, and a cyclohexyl group. $R^2$ is preferably an isopropyl group, a sec-butyl group, or an isobutyl group.

When $R^1$ or $R^2$ has an asymmetric carbon, the compound represented by Formula (1) contains any one of the resulting optical isomers or a mixture of the optical isomers in any proportion.

The compound represented by Formula (1) is useful as a fragrance and fragrance ingredient, has a floral aroma, and in addition, simultaneously exhibits an aroma of a fruity note, woody note, spicy note, green note, mint note, or the like depending on the difference in $R^1$ or $R^2$.

$R^1$ is preferably a methyl group.

$R^1$ is preferably an ethyl group.

$R^2$ is preferably an isopropyl group.

$R^2$ is preferably a sec-butyl group.

$R^2$ is preferably an isobutyl group.

Particularly preferably, $R^1$ is a methyl group and $R^2$ is an isopropyl group.

Particularly preferably, $R^1$ is an ethyl group and $R^2$ is an isopropyl group.

Particularly preferably, $R^1$ is a methyl group and $R^2$ is a sec-butyl group.

Particularly preferably, $R^1$ is an ethyl group and $R^2$ is a sec-butyl group.

Particularly preferably, $R^1$ is a methyl group and $R^2$ is an isobutyl group.

Particularly preferably, $R^1$ is an ethyl group and $R^2$ is an isobutyl group.

In the present invention, the compound represented by Formula (1) is exemplified by a compound represented by any of Formulas (1-1) to (1-34) below, and a particularly preferred compound is a compound represented by any of Formulas (1-4), (1-5), (1-8), (1-12), (1-13), and (1-16) below.

[Chem. 4]

(1-1)

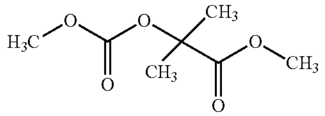

(1-2)

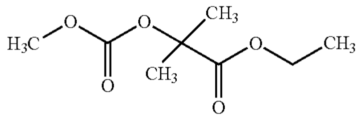

(1-3)

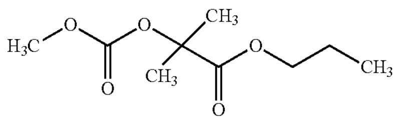

(1-4)

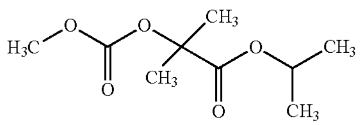

-continued
(1-5)
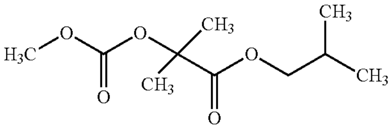
(1-6)
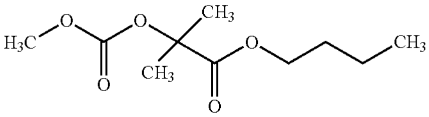
(1-7)
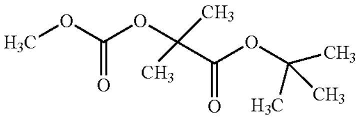
(1-8)
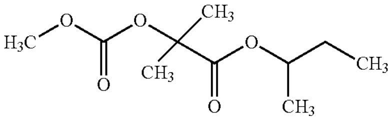
(1-9)
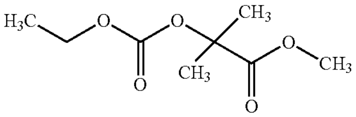
(1-10)
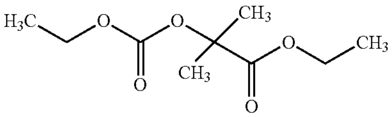
(1-11)
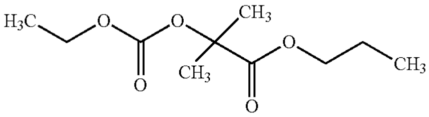
(1-12)
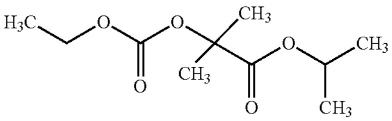
(1-13)
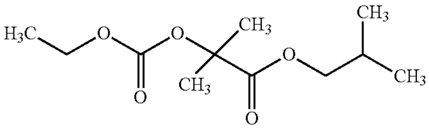
(1-14)
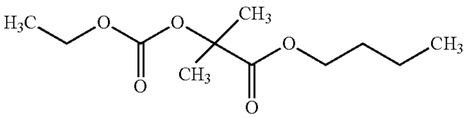
(1-15)
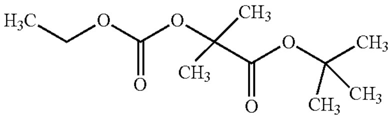
(1-16)
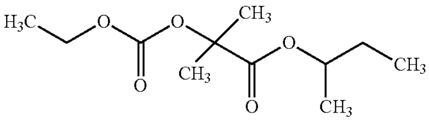
-continued
[Chem. 5]
(1-17)
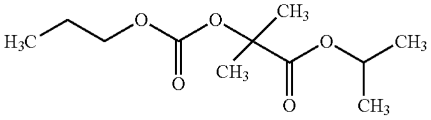
(1-18)
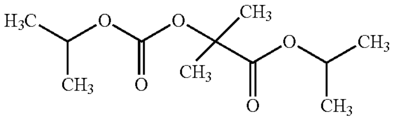
(1-19)
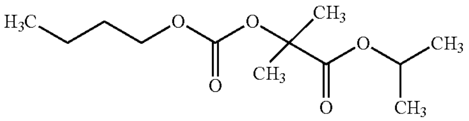
(1-20)
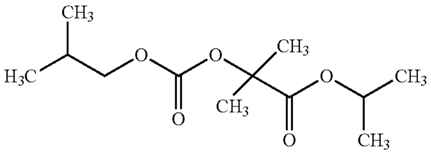
(1-21)
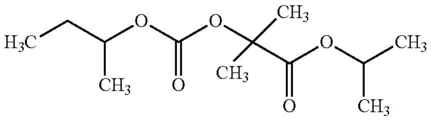
(1-22)
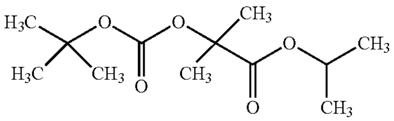
(1-23)
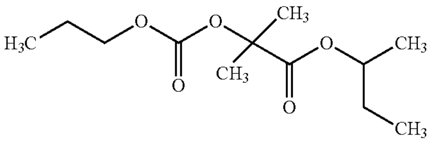
(1-24)
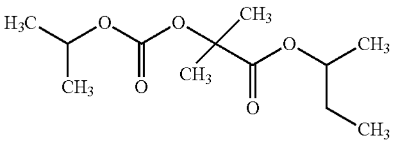
(1-25)
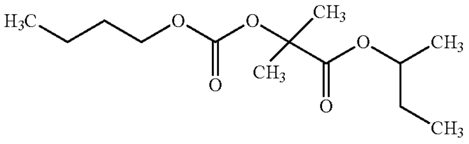
(1-26)
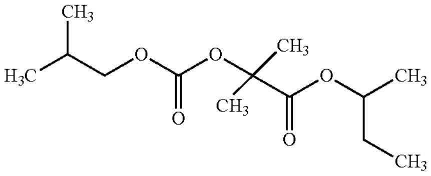

-continued (1-27)

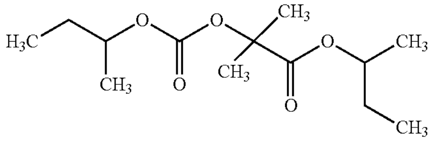

(1-28)

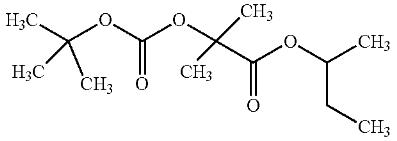

[Chem. 6]

(1-29)

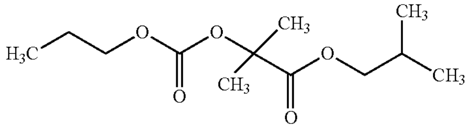

(1-30)

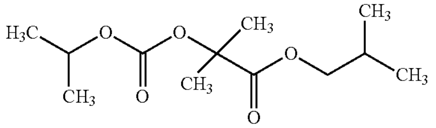

(1-31)

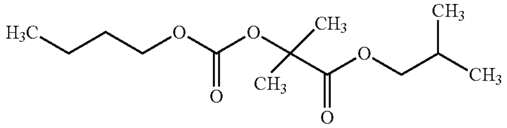

(1-32)

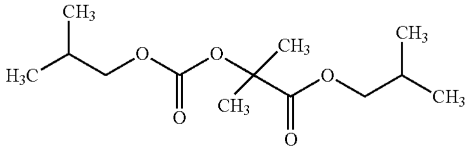

(1-33)

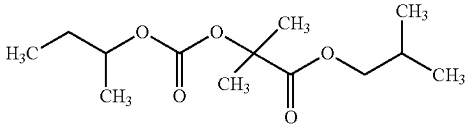

(1-34)

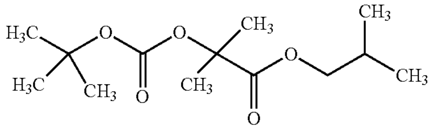

The compound represented by Formula (1) itself has an excellent aroma as described later and thus is useful as a fragrance. Also, in general, a fragrance is rarely used alone and is often used in a fragrance formulation (fragrance composition) formed by blending a plurality of fragrances according to the purpose. The compound represented by Formula (1) is useful as a fragrance (also referred to as a "fragrance ingredient") to be blended in a fragrance formulation (fragrance composition), and the fragrance composition of the present invention contains the compound represented by Formula (1) as an active ingredient. As the fragrance, one of the compounds represented by Formula (1) above may be used alone, or two or more of the compounds may be used in combination.

In addition, this does not exclude that the compound represented by Formula (1) may contain a small amount of impurities, by-products, contaminants, or the like, within a range that does not impair the effects of the present invention.

The compound represented by Formula (1) has a floral aroma as well as an aroma of a fruity note, woody note, spicy note, green note, mint note, or the like, and also has excellent diffusivity. The compound represented by Formula (1) may be used alone as a fragrance and added to various perfumes and cosmetics, healthcare and sanitary materials as well as pharmaceutical products, household goods, foods, and the like, to impart an aroma to those products. In addition, the compound represented by Formula (1) may be mixed with another fragrance ingredient or the like to prepare a fragrance composition (fragrance formulation) described later, and this composition may be blended in various products to impart an aroma to those products. Among these, from the viewpoint of obtaining an intended aroma, the compound represented by Formula (1) is preferably blended in a fragrance composition as a fragrance ingredient to prepare a fragrance composition containing the compound represented by Formula (1) as an active ingredient, and the fragrance composition is preferably blended in a product to perfume the product.

<Fragrance Composition>

The fragrance composition (fragrance formulation) of the present invention contains the compound represented by Formula (1) as an active ingredient. The fragrance composition is any composition containing at least one compound represented by Formula (1) and is not particularly limited and may contain two or more compounds represented by Formula (1).

The fragrance composition of the present invention contains the compound represented by Formula (1) as an active ingredient; however other components are not particularly limited, and the fragrance composition preferably further contains another fragrance ingredient (hereinafter also referred to as the "known fragrance").

The "fragrance composition (fragrance formulation)" is a composition to be added to various perfumes and cosmetics, pharmaceutical products, foods, beverages, and the like to impart an aroma to these products, or a composition used as it is in a perfume or the like. The fragrance composition may contain an additive, such as a solvent, as necessary in addition to the known fragrance.

The amount of the compound represented by Formula (1) to be blended depends on the type of the compound, the type of intended aroma, the intensity of the aroma, and the like. The amount of the compound represented by Formula (1) in the fragrance composition is preferably 0.001 mass % or greater, more preferably 0.01 mass % or greater, even more preferably 0.1 mass % or greater, and preferably 90 mass % or less, more preferably 70 mass % or less, and even more preferably 50 mass % or less.

The known fragrance is not particularly limited as long as it is a known fragrance component, and a wide range of fragrances can be used. For example, one, or two or more of the following fragrances can be selected and used at any mixing ratio.

Examples thereof include hydrocarbons such as limonene, α-pinene, β-pinene, terpinene, cedrene, longifolene, and valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-t-butylcyclohexanol, 4-methyl-2-(2-methylpropyl)tetrahydro- 2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol; phenols such as eugenol, thymol, and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobornyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and FRUITATE; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, and cyclohexadecenone; acetals and ketals such as acetoaldehyde ethylphenylpropyl acetal, citraldiethyl acetal, phenylacetoaldehyde glycerin acetal, and ethylacetoacetate ethyleneglycol ketals; ethers such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2,1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, sandalwood, vetiver, patchouli, and labdanum; and other fragrance materials such as synthetic fragrances.

In addition, the fragrance composition may also contain, as a component other than the fragrance ingredient, a surfactant, such as polyoxyethylene lauryl sulfate ether; a solvent, such as dipropylene glycol, diethyl phthalate, ethylene glycol, propylene glycol, methyl myristate, or triethyl citrate; an antioxidant; or a colorant.

The compound represented by Formula (1) has a floral aroma as well as an aroma of a fruity note, woody note, spicy note, green note, mint note, or the like and thus can impart a natural fruity note, woody note, spicy note, green note, or mint note together with a floral note in combination with the known fragrance. Thus, the compound is usefully added to various perfumes and cosmetics, healthcare and sanitary materials as well as to pharmaceutical products, household goods, foods, and the like to impart an aroma to these products.

Examples of the products to which the fragrance composition containing the compound represented by Formula (1) can be added to impart an aroma and improve the aroma of such a product can include various products, such as perfumes and cosmetics, health and sanitary materials, miscellaneous goods, beverages, foods, quasi-pharmaceutical products, and pharmaceutical products, and the fragrance composition can be used as an aroma component of, for example, fragrance products, such as perfumes and colognes; hair cosmetics, such as shampoos, rinses, hair tonics, hair creams, mousses, gels, pomades, sprays, and others; skin cosmetics, such as skin lotions, essences, creams, milky lotions, packs, foundations, face powders, lipsticks, and various make-up products; various health and sanitary detergents, such as dish washing detergents, laundry detergents, softeners, disinfecting detergents, anti-odor detergents, indoor fragrances, furniture cares, glass cleaners, furniture cleaners, floor cleaners, disinfectants, insecticides, bleaching agents, bactericides, repellants, and others; quasi-pharmaceutical products, such as toothpastes, mouthwashes, bath additives, antiperspirant products, and permanent liquids; miscellaneous goods, such as toilet paper and tissue paper; pharmaceutical products; and foods.

The amount of the fragrance composition blended in the product is not particularly limited, and the amount of the fragrance composition blended can be selected over a wide range, depending on the type, nature, and sensory benefits of the product to be perfumed. For example, the amount may be 0.00001 mass % or greater, preferably 0.0001 mass % or greater, more preferably 0.001 mass % or greater. In the case of a fragrance such as perfume or the like, for example, the amount may be 100 mass %, preferably 80 mass % or less, more preferably 60 mass % or less, and even more preferably 40 mass % or less.

[Compound Represented by Formula (2)]

The compound of the present invention is represented by Formula (2). The compound represented by Formula (2) is hereinafter also referred to as the "isobutyric acid ester of the present invention".

[Chem. 7]

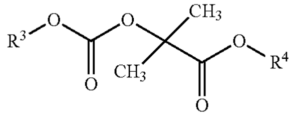

(2)

where in Formula (2), $R^3$ represents a linear, branched, or cyclic alkyl group having from 1 to 4 carbon(s); and $R^4$ represents a linear, branched, or cyclic alkyl group having from 1 to 6 carbon(s), with the proviso that a compound where $R^3$ is an ethyl group and $R^4$ is a methyl group, a compound where $R^3$ is an ethyl group and $R^4$ is an ethyl group, and a compound where $R^3$ is a n-butyl group and $R^4$ is an ethyl group are excluded.

Examples of $R^3$ in Formula (2) specifically include a methyl group, an ethyl group, a n-propyl group, an isopropyl group, a n-butyl group, an isobutyl group (2-methylpropyl group), a sec-butyl group (1-methylpropyl group), a tert-butyl group, a cyclopropyl group, and a cyclobutyl group. $R^3$ is preferably a methyl group, an ethyl group, a n-propyl group, an isopropyl group, a n-butyl group, or an isobutyl group (2-methylpropyl group), and more preferably a methyl group or an ethyl group.

Examples of $R^4$ in Formula (2) specifically include a methyl group, an ethyl group, a n-propyl group, an isopropyl group, a n-butyl group, an isobutyl group (2-methylpropyl group), a sec-butyl group (1-methylpropyl group), a tert-butyl group, a n-pentyl group, a 1-methylbutyl group (2-pentyl group), a 2-methylbutyl group, a 3-methylbutyl group, a neopentyl group (2,2-dimethylpropyl group), a 2-methylbutan-2-yl group, a 1-ethylpropyl group (3-pentyl group), a 3-methylbutan-2-yl group, a n-hexyl group, a 1-methylpentyl group (2-hexyl group), a 2-methylpentyl group, a 3-methylpentyl group, a 4-methylpentyl group, a 2-methylpentan-2-yl group, a 2,2-dimethylbutyl group, a 3,3-dimethylbutyl group, a 3-methylpentan-2-yl group, a 2,3-dimethylbutyl group, a 4-methylpentan-2-yl group, a 3-hexyl group, a 2-ethylbutyl group, a 2,3-dimethylbutan-2-yl group, a 3,3-dimethylbutan-2-yl group, a 4-methylpentan-3-yl group, a cyclopropyl group, a cyclobutyl group, a cyclopentyl group, and a cyclohexyl group. $R^4$ is preferably an isopropyl group, a sec-butyl group, or an isobutyl group.

However, a compound where $R^3$ is an ethyl group and $R^4$ is a methyl group in Formula (2), a compound where $R^3$ is an ethyl group and $R^4$ is an ethyl group, and a compound where $R^3$ is a n-butyl group and $R^4$ is an ethyl group are excluded.

When $R^3$ or $R^4$ has an asymmetric carbon, the compound represented by Formula (2) contains any one of the resulting optical isomers or a mixture of the optical isomers in any proportion.

For the isobutyric acid ester of the present invention, $R^3$ in Formula (2) is preferably a methyl group or an ethyl group. In addition, $R^4$ is preferably an isopropyl group, a sec-butyl group, or an isobutyl group. However, a compound where $R^3$ is an ethyl group and $R^4$ is a methyl group, a compound where $R^3$ is an ethyl group and $R^4$ is an ethyl group, and a compound where $R^3$ is a n-butyl group and $R^4$ is an ethyl group are excluded.

That is, the isobutyric acid ester of the present invention is particularly preferably a compound below.

$R^3$ is preferably a methyl group.

$R^3$ is preferably an ethyl group. However, a compound where $R^4$ is a methyl group or an ethyl group is excluded.

$R^4$ is preferably an isopropyl group.

$R^4$ is preferably a sec-butyl group.

$R^4$ is preferably an isobutyl group.

Particularly preferably, $R^3$ is a methyl group and $R^4$ is an isopropyl group.

Particularly preferably, $R^3$ is an ethyl group and $R^4$ is an isopropyl group.

Particularly preferably, $R^3$ is a methyl group and $R^4$ is a sec-butyl group.

Particularly preferably, $R^3$ is an ethyl group and $R^4$ is a sec-butyl group.

Particularly preferably, $R^3$ is a methyl group and $R^4$ is an isobutyl group.

Particularly preferably, $R^3$ is an ethyl group and $R^4$ is an isobutyl group.

The isobutyric acid ester of the present invention is preferably a compound represented by any of Formulas (2-1) to (2-26) below and particularly preferably a compound represented by any of Formulas (2-4), (2-5), (2-8), (2-10), (2-11), and (2-14) below.

[Chem. 8]

(2-1)

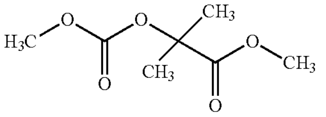

(2-2)

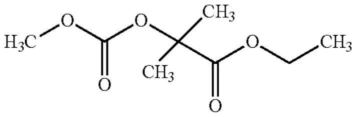

(2-3)

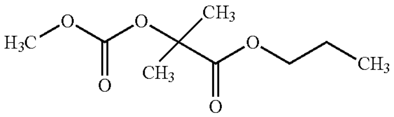

(2-4)

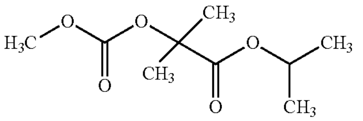

(2-5)

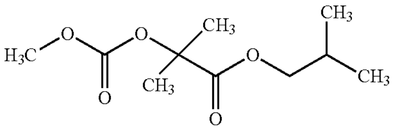

(2-6)

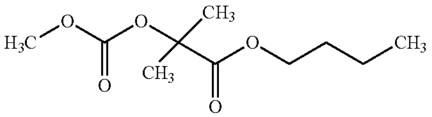

(2-7)

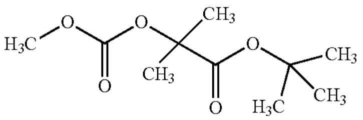

(2-8)

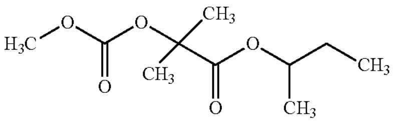

(2-9)

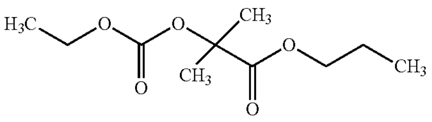

(2-10)

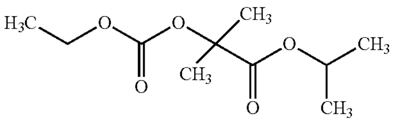

(2-11)

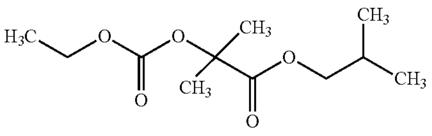

(2-12)

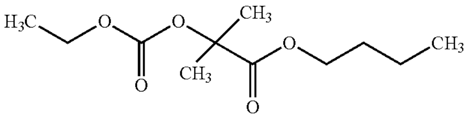

-continued (2-13)

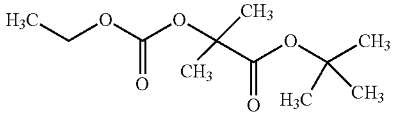

(2-14)

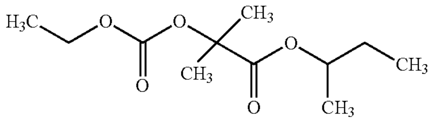

[Chem. 9]

(2-15)

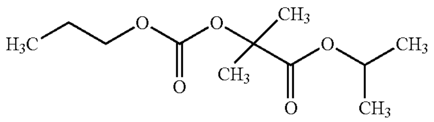 [SMILES: CCCOC(=O)OC(C)(C)C(=O)OC(C)C]

(2-16)

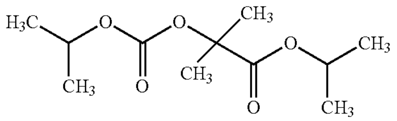

(2-17)

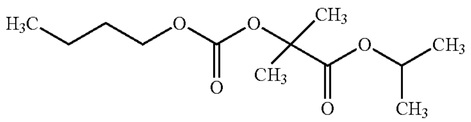

(2-18)

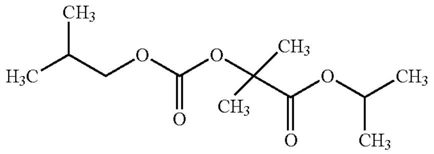

(2-19)

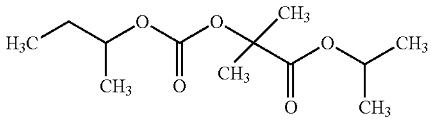

(2-20)

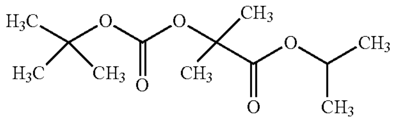

(2-21)

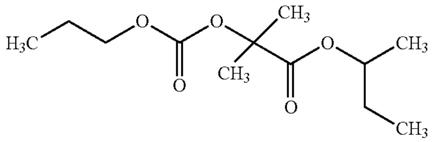

(2-22)

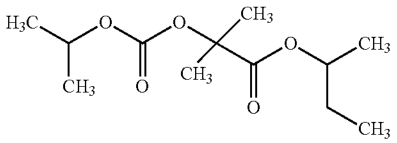

(2-23)

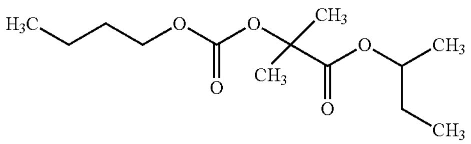

-continued (2-24)

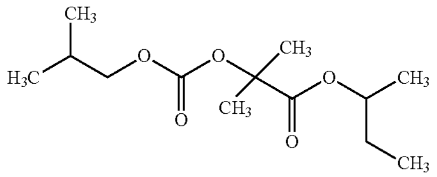

(2-25)

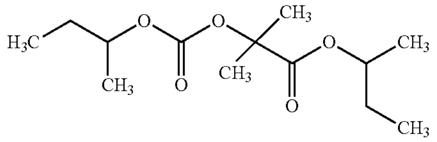

(2-26)

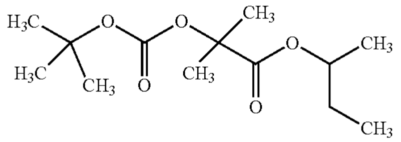

The isobutyric acid ester of the present invention is a compound represented by Formula (2), with the proviso that the following are excluded: a compound where $R^3$ is an ethyl group and $R^4$ is a methyl group, a compound where $R^3$ is an ethyl group and $R^4$ is an ethyl group, and a compound where $R^3$ is a n-butyl group and $R^4$ is an ethyl group. Thus, the isobutyric acid ester according to the present invention is useful by itself as a fragrance and is also useful as an active ingredient for a fragrance composition.

[Method for Producing Isobutyric Acid Ester According to Embodiment of Present Invention and Compound Represented by Formula (1)]

The methods for producing the isobutyric acid ester of the present invention represented by Formula (2) and the compound represented by Formula (1) are not particularly limited and are appropriately selected from known methods.

For example, the isobutyric acid ester having a carbonate group at the α-position can be produced by reacting an α-hydroxyisobutyric acid ester or its alkali metal alkoxide with a halogenoformate. The reaction formula for this reaction is shown in Formula (3) below:

[Chem. 10]

(3)

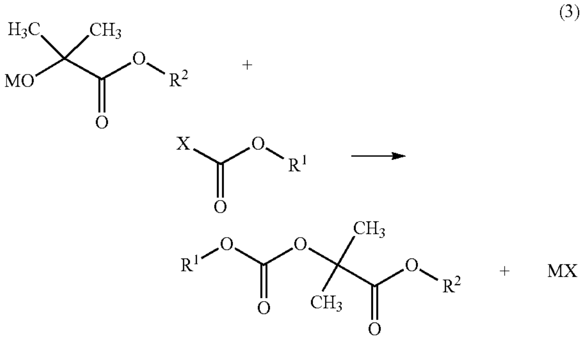

where in Formula (3), $R^1$ represents a linear, branched, or cyclic alkyl group having from 1 to 4 carbon(s); and $R^2$ represents a linear, branched, or cyclic alkyl group having from 1 to 6 carbon(s); M represents a hydrogen atom or an alkali metal atom, such as sodium, potassium, or cesium; and X represents a halogen atom, such as chlorine, bromine, or iodine.

In addition, the isobutyric acid ester having a carbonate group at the α-position can be produced by transesterification reaction of an α-hydroxyisobutyric acid ester and a carbonate ester in the presence of a catalyst. The reaction formula of this reaction is shown in Formula (4) below:

[Chem. 11]

(4)

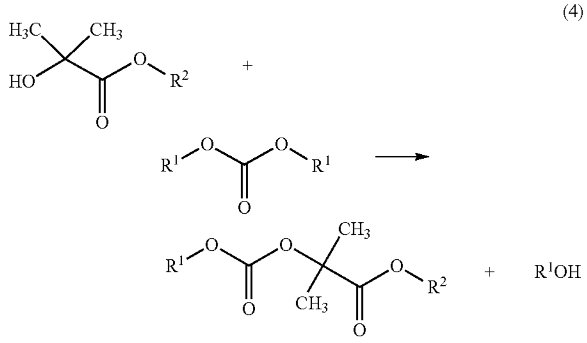

where in Formula (4), $R^1$ represents a linear, branched, or cyclic alkyl group having from 1 to 4 carbon(s); and $R^2$ represents a linear, branched, or cyclic alkyl group having from 1 to 6 carbon(s).

In addition, an intended isobutyric acid ester having a carbonate group at the α-position can be produced by transesterification reaction of a different type of isobutyric acid ester having a carbonate group at the α-position and an alcohol in the presence of a catalyst. The reaction formula of this reaction is shown in Formula (5) below:

[Chem. 12]

(5)

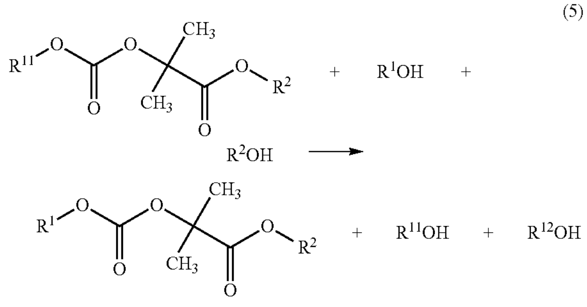

where in Formula (5), $R^1$ represents a linear, branched, or cyclic alkyl group having from 1 to 4 carbon(s); $R^2$ represents a linear, branched, or cyclic alkyl group having from 1 to 6 carbon(s); $R^{11}$ represents a group different from $R^1$; and $R^{12}$ represents a group different from $R^2$.

For the catalyst, reaction method, reaction conditions, reaction apparatus, and the like, to be used in these reactions, a catalyst, a reaction method, reaction conditions, and a reaction apparatus known in the art can be used without any particular limitation. In addition, as to the methods of purifying the resulting isobutyric acid ester of the present invention represented by Formula (2) and the compound represented by Formula (1), known purification methods can be employed without any particular limitation.

EXAMPLES

Hereinafter, the present invention will be described in further detail with reference to examples, but the present invention is not limited to these examples.

The reaction performance was evaluated according to the following expression.

Reaction yield (%)=[(number of moles of product ester in reaction solution)/(number of moles of raw material ester in solution fed)]×100%

<Gas Chromatography Analysis (GC Analysis)>

Apparatus: "GC-2010" (available from Shimadzu Corporation, trade name)

Detector: FID

Column: "DB-1" (capillary column available from J&W Scientific, Inc., trade name) (0.25 mmφ×60 m×0.25 μm)

<NMR Spectral Analysis>

Identification of the ester was performed by $^1$H-NMR measurement and $^{13}$C-NMR measurement. The measurement conditions are shown below.

Apparatus: "ECA500" (available from JEOL Ltd., trade name)

($^1$H-NMR)

Nuclide: $^1$H

Measurement frequency: 500 MHz

Measurement sample: 5% $CDCl_3$ solution ($^{13}$C-NMR)

Nuclide: $^{13}$C

Measurement frequency: 125 MHz

Measurement sample: 5% $CDCl_3$ solution

<Gas Chromatograph-Mass Spectrum Analysis (GC-MS Analysis)>

Identification of the compounds was also performed by determining the molecular weight by GC-MS measurement (chemical ionization method [CI+], high-resolution mass spectrometry [millimass]). The measurement conditions are shown below.

GC apparatus: "Agilent 7890A" (available from Agilent Technologies, Inc., trade name)

GC measurement conditions

Column: "DB-1" (capillary column available from J&W Scientific, Inc., trade name) (0.25 mmφ×30 m×0.25 μm)

MS apparatus: "JMS-T100GCV" (available from JEOL Ltd., trade name)

MS measurement conditions, chemical ionization method

Detector conditions: 200 eV, 300 μA

Reagent gas: isobutane

The exact mass values of fragments detected in the protonated state by the chemical ionization method and the chemical composition formula thus attributed were described.

<Product Isolation by Chromatography>

For product isolation by chromatography, materials described below were used.

Filler: "Wakogel C-200" (available from FUJIFILM Wako Pure Chemical Corporation, trade name)

Development solvent: ethyl acetate-hexane

Reference Example 1: Synthesis of Isopropyl α-Hydroxyisobutyrate

A 300-mL glass flask equipped with a distillation tube was charged with 88.7 g of methyl α-hydroxyisobutyrate (available from Mitsubishi Gas Chemical Company, Inc.), 106.1 g of isopropanol (available from FUJIFILM Wako Pure Chemical Corporation), and 0.21 g of sodium methoxide (available from FUJIFILM Wako Pure Chemical Corporation). A transesterification reaction was performed under normal pressure with heating and refluxing. The reaction was performed for 48 hours while methanol produced was extracted out of the system. As a result, isopropyl α-hydroxyisobutyrate was obtained by a reaction of Formula (6) below with a reaction yield of 98.4%. Water was added to the reaction system to deactivate the catalyst, then the reaction system was distilled under reduced pressure, and 77.7 g of isopropyl α-hydroxyisobutyrate (purity by GC analysis (hereinafter also referred to as GC purity): 99.6%) was obtained as a distillate at 40 mmHg and 65° C.

[Chem. 13]

(6)

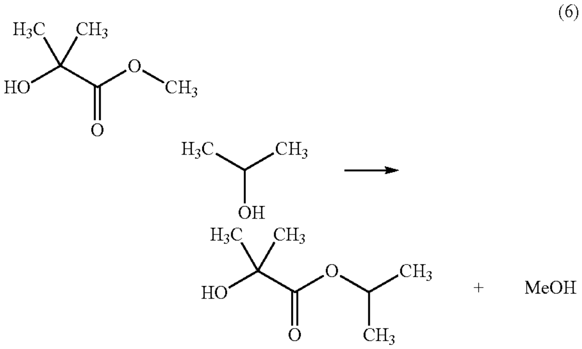

Reference Examples 2 to 3: Syntheses of Various α-Hydroxyisobutyric Acid Esters Using the same reaction apparatus as in Reference Example 1, an appropriate amount of methyl α-hydroxyisobutyrate (available from Mitsubishi Gas Chemical Company, Inc.) was transesterified with an alcohol of various types (isobutanol or sec-butanol) in the presence of a suitable catalyst, such as a titanium tetraalkoxide and/or a sodium alkoxide, and in some cases in the co-presence of a solvent, such as hexane or toluene, under appropriate reaction conditions with heating. The transesterification reaction was completed while methanol produced by the reaction was extracted out of the system by distillation or through azeotrope with a reaction solvent under the reaction conditions. The same separation operation as in Reference Example 1 was performed to obtain each of the following α-hydroxyisobutyric acid ester. The GC purity of the resulting isobutyric acid ester was also described.

Isobutyl α-hydroxyisobutyrate (GC purity: 99.6%)

sec-Butyl α-hydroxyisobutyrate (GC purity: 99.6%)

Example 1: Synthesis of Isopropyl α-(Methoxycarbonyl)Oxyisobutyrate

A 50-mL glass flask equipped with a stirrer and a dropping device was charged with 5.0 g of isopropyl α-hydroxyisobutyrate synthesized in Reference Example 1, 5.6 g of N-methylimidazole (available from Tokyo Chemical Industry Co., Ltd.), and 6.5 mL of dichloromethane (available from FUJIFILM Wako Pure Chemical Corporation) and cooled to 0° C. A solution of 4.9 g of methyl chloroformate (available from Tokyo Chemical Industry Co., Ltd.) dissolved in 6.5 mL of dichloromethane (available from FUJIFILM Wako Pure Chemical Corporation) was slowly added dropwise with stirring. After the end of the drop-wise addition, stirring was continued for 2 hours while the temperature was kept at 0° C. Cooling was then stopped, stirring was continued while the temperature was slowly returned to ordinary temperature, and the reaction was continued for 15 hours. GC analysis of the reaction solution revealed that isopropyl α-(methoxycarbonyl)oxyisobutyrate was obtained with a reaction yield of 81% by the reaction of Formula (6) below. The reaction solution was then washed twice with a 10% aqueous sodium bicarbonate solution and twice with a saturated aqueous ammonium chloride solution, dried with sodium sulfate, then concentrated, and 3.2 g (GC purity: 99.6%) of isopropyl α-(methoxycarbonyl)oxyisobutyrate was obtained with a column chromatograph. The results of the NMR spectral analysis and GC-MS analysis of the product are shown below.

(Isopropyl α-(methoxycarbonyl)oxyisobutyrate)

$^1$H NMR (500 MHz, $CDCl_3$) δ1.251 (6H, d, J=6.0 Hz), 1.590 (6H, s), 3.768 (3H, s), 5.070 (1H, sept (7), J=6.25 Hz)

$^{13}$C NMR (125 MHz, $CDCl_3$) δ21.66, 24.55, 54.77, 69.11, 80.42, 154.26, 171.75

Exact. Mass 205.10847 ($C_9H_{16}O_5$, parent peak), 129.09197 ($C_7H_{12}O_2$)

[Chem. 14]

(7)

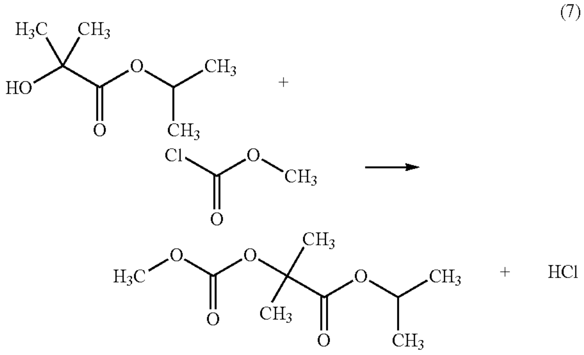

Examples 2 to 6: Syntheses of Various Isopropyl α-(Alkoxycarbonyl)Oxyisobutyrates A reaction was performed using a reaction device similar to that of Reference Example 1 and using appropriate amounts of isopropyl α-hydroxyisobutyrate prepared in Reference Example 1, a chloroformate of various types (ethyl chloroformate, n-propyl chloroformate, isopropyl chloroformate, n-butyl chloroformate, or isobutyl chloroformate; all available from Tokyo Chemical Industry Co., Ltd.), N-methylimidazole (available from Tokyo Chemical Industry Co., Ltd.), and dichloromethane (available from FUJIFILM Wako Pure Chemical Corporation). Various isopropyl α-(alkoxycarbonyl)oxyisobutyrates below were each obtained with a column chromatograph in the same manner as in Example 1. The GC purity of the resulting esters and the results of NMR spectral analysis and GC-MS analysis are shown in combination.

(Isopropyl α-(Ethoxycarbonyl)Oxyisobutyrate)

GC purity: 99.7%

$^1$H NMR (500 MHz, $CDCl_3$) δ1.251 (6H, d, J=6.5 Hz), 1.315 (3H, t, J=7.5 Hz), 1.591 (6H, s), 4.179 (2H, q, J=7.0 Hz), 5.070 (1H, spt (7), J=6.25 Hz)

$^{13}$C NMR (125 MHz, $CDCl_3$) δ14.34, 21.67, 24.57, 64.06, 69.04, 80.21, 153.64, 171.83 Exact. Mass 219.12564 ($C_{10}H_{18}O_5$, parent peak)

(Isopropyl α-(n-Propoxycarbonyl)Oxyisobutyrate)

GC purity: 99.9%

$^1$H NMR (500 MHz, $CDCl_3$) δ0.97 (3H, t, J=7.5 Hz), 1.25 (6H, d, J=6.5 Hz), 1.59 (6H, s), 1.70 (2H, qt, J=6.5, 7.5 Hz), 4.08 (2H, t, J=6.5 Hz), 5.07 (1H, sept, J=6.5 Hz)

$^{13}C$ NMR (125 MHz, $CDCl_3$) δ10.12, 21.51, 21.96, 24.43, 68.87, 69.51, 80.04, 153.65, 171.67

Exact. Mass 233.13737 ($C_{11}H_{20}O_5$, parent peak)

(Isopropyl α-(Isopropoxycarbonyl)Oxyisobutyrate)

GC purity: 99.3%

$^1H$ NMR (500 MHz, $CDCl_3$) δ1.249 (6H, d, J=6.5 Hz), 1.305 (6H, d, J=6.5 Hz), 1.587 (6H, s), 4.844 (1H, sept (7), J=6.25 Hz), 5.068 (1H, sept (7), J=6.25 Hz)

$^{13}C$ NMR (125 MHz, $CDCl_3$) δ21.69, 21.85, 24.60, 69.00, 72.12, 80.07, 153.16, 171.92

Exact. Mass 233.13768 ($C_{11}H_{20}O_5$, parent peak), 129.09123 ($C_7H_{12}O_2$)

(Isopropyl α-(n-Butoxycarbonyl)Oxyisobutyrate)

GC purity: 99.8%

$^1H$ NMR (500 MHz, $CDCl_3$) δ0.94 (3H, t, J=7.5 Hz), 1.25 (6H, d, J=6.5 Hz), 1.36-1.46 (2H, m), 1.59 (6H, s), 1.62-1.69 (2H, m), 4.12 (2H, t, J=6.5 Hz), 5.07 (1H, sept, J=6.5 Hz)

$^{13}C$ NMR (125 MHz, $CDCl_3$) δ13.60, 18.85, 21.52, 24.43, 30.62, 67.81, 68.87, 80.04, 153.65, 171.70

Exact. Mass 247.15379 ($C_{12}H_{22}O_5$, parent peak)

(Isopropyl α-(Isobutoxycarbonyl)Oxyisobutyrate)

GC purity: 99.5%

$^1H$ NMR (500 MHz, $CDCl_3$) δ0.95 (6H, d, J=7.0 Hz), 1.24 (6H, d, J=6.5 Hz), 1.59 (6H, s), 1.94-2.03 (1H, m), 3.90 (2H, d, J=6.5 Hz), 5.06 (1H, sept, J=6.5 Hz)

$^{13}C$ NMR (125 MHz, $CDCl_3$) δ18.85, 21.51, 24.43, 27.74, 68.87, 73.98, 80.03, 153.73, 171.72

Exact. Mass 247.15746 ($C_{12}H_{22}O_5$, parent peak)

Example 7: Synthesis of Isobutyl α-(Ethoxycarbonyl)Oxyisobutyrate

A reaction was performed using a reaction device similar to that of Example 1 and using appropriate amounts of isobutyl α-hydroxyisobutyrate prepared in Reference Example 2, ethyl chloroformate (available from Tokyo Chemical Industry Co., Ltd.), N-methylimidazole (available from Tokyo Chemical Industry Co., Ltd.), and dichloromethane (available from FUJIFILM Wako Pure Chemical Corporation). Isobutyl α-(ethoxycarbonyl)oxyisobutyrate below was obtained with a column chromatograph in the same manner as in Example 1. The GC purity of the resulting esters and the results of NMR spectral analysis and GC-MS analysis are shown in combination.

(Isobutyl α-(Ethoxycarbonyl)Oxyisobutyrate)

GC purity: 99.5%

$^1H$ NMR (500 MHz, $CDCl_3$) δ0.94 (6H, d, J=7.0 Hz), 1.31 (3H, t, J=7.0 Hz), 1.61 (6H, s), 1.96 (1H, nonatet, J=7.0 Hz), 3.93 (2H, d, J=7.0 Hz), 4.17 (1H, q, J=7.0 Hz), 4.18 (1H, q, J=7.0 Hz)

$^{13}C$ NMR (125 MHz, $CDCl_3$) δ14.16, 18.92, 24.57, 27.62, 63.98, 71.47, 80.14, 153.54, 172.27

Exact. Mass 233.13845 ($C_{11}H_{20}O_5$, parent peak), 143.10793 ($C_8H_{14}O_2$)

Example 8: Synthesis of s-Butyl α-(Ethoxycarbonyl)Oxyisobutyrate

A reaction was performed using a reaction device similar to that of Example 1 and using appropriate amounts of sec-butyl α-hydroxyisobutyrate prepared in Reference Example 3, ethyl chloroformate (available from Tokyo Chemical Industry Co., Ltd.), N-methylimidazole (available from Tokyo Chemical Industry Co., Ltd.), and dichloromethane (available from FUJIFILM Wako Pure Chemical Corporation). sec-Butyl α-(ethoxycarbonyl)oxyisobutyrate below was obtained with a column chromatograph in the same manner as in Example 1. The GC purity of the resulting esters and the results of NMR spectral analysis and GC-MS analysis are shown in combination.

(Sec-Butyl α-(Ethoxycarbonyl)Oxyisobutyrate)

GC purity: 99.8%

$^1H$ NMR (500 MHz, $CDCl_3$) δ0.90 (3H, t, J=7.5 Hz), 1.22 (3H, d J=6.0 Hz), 1.31 (3H, t, J=7.0 Hz), 1.56-1.65 (2H, m), 1.60 (6H, s), 4.18 (1H, q, J=7.0 Hz), 4.18 (1H, q, J=7.0 Hz), 4.90 (1H, sext, J=6.5 Hz).

$^{13}C$ NMR (125 MHz, $CDCl_3$) δ9.49, 14.16, 19.09, 24.42, 24.51, 28.59, 63.89, 73.44, 80.11, 153.45, 171.78

Exact. Mass 233.14004 ($C_{11}H_{20}O_5$, parent peak), 177.07780 ($C_7H_{12}O_5$)

The various isobutyric acid esters having a carbonate group at the α-position obtained by the methods described above were evaluated for aroma by a perfumer. The results are shown in Table 1.

TABLE 1

| | Structural formula | Aroma evaluation |
|---|---|---|
| Example 1 | 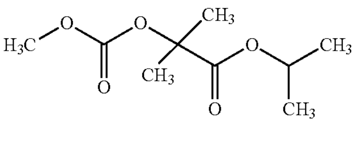 | Rose-like floral aroma<br>Violet-like floral aroma<br>Floral green aroma<br>Mint-like aroma |
| Example 2 | 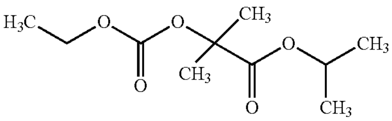 | Violet-like floral aroma<br>Iris-like floral and woody aroma<br>Fresh fruity aroma<br>Woody aroma<br>Mint-like aroma |
| Example 3 | 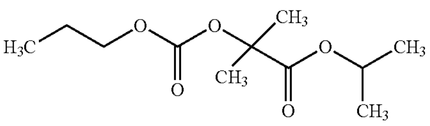 | Floral and balsamic aroma<br>Coconut-like fruity aroma<br>Iris-like floral and woody aroma<br>Rose-like floral aroma<br>Mint-like aroma |

TABLE 1-continued

| | Structural formula | Aroma evaluation |
|---|---|---|
| Example 4 | 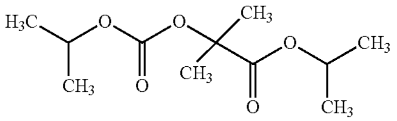 [SMILES: CC(C)OC(=O)OC(C)(C)C(=O)OC(C)C] | Fruity aroma<br>Rose-like floral aroma<br>Woody aroma<br>Jasmine-like spicy aroma |
| Example 5 | 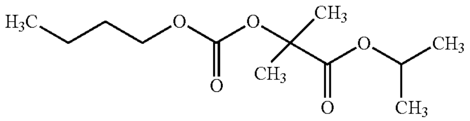 [SMILES: CCCCOC(=O)OC(C)(C)C(=O)OC(C)C] | Violet-like floral aroma<br>Rose-like floral aroma<br>Woody aroma<br>Mint-like aroma |
| Example 6 | 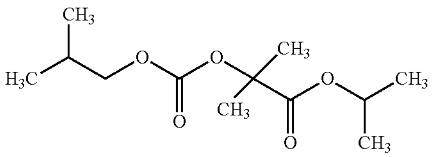 [SMILES: CC(C)COC(=O)OC(C)(C)C(=O)OC(C)C] | Fruity aroma<br>White floral aroma<br>Rose-like green aroma<br>Spicy aroma |
| Example 7 | 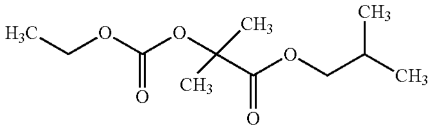 [SMILES: CCOC(=O)OC(C)(C)C(=O)OCC(C)C] | Woody aroma<br>Woody umber aroma<br>Floral green aroma<br>Coconut-like fruity aroma<br>Rose-like fresh floral aroma |
| Example 8 | 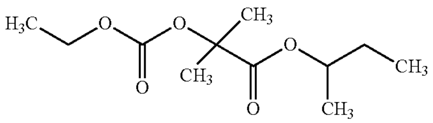 [SMILES: CCOC(=O)OC(C)(C)C(=O)OC(C)CC] | Rose-like floral aroma<br>Jasmine-like spicy aroma<br>Mint-like aroma<br>Apple-like fruity aroma |

Example 9: Fragrance Composition for Fruity Floral Type Shower Gel

A fragrance composition was formulated in which 75 parts by mass of isopropyl α-(ethoxycarbonyl)oxyisobutyrate obtained in Example 2 was added to 925 parts by mass of a fragrance composition with a composition shown in Table 2.

Isopropyl α-(ethoxycarbonyl)oxyisobutyrate of Example 2 was added to the fragrance composition with the composition described in Table 2, and this composition increased the intensity as well as diffusivity of the scent. This composition brought out spread and integrity of the scent and was able to impart a fresher fruity floral impression to the composition according to aroma evaluation by a perfumer. As a result, a novel fragrance composition for a fruity floral type shower gel was able to obtain.

TABLE 2

| Blend ingredients | parts by mass |
|---|---|
| Aldehyde C-12 lauric | 2.0 |
| Allyl amyl glycolate | 5.0 |
| Allyl heptanoate | 3.0 |
| Iso E Super | 160.0 |
| Ambroxan | 0.4 |
| Bacdanol | 5.0 |
| Benzaldehyde | 0.1 |
| Benzyl acetate | 90.0 |
| Cedarwood Virginia | 65.0 |
| cis-3-Hexenol | 1.6 |
| cis-3-Hexenyl isobutyrate | 2.0 |
| cis-3-Hexenyl salicylate | 10.0 |
| α-Damascone | 2.7 |
| γ-Decalactone | 1.3 |

TABLE 2-continued

| Blend ingredients | parts by mass |
|---|---|
| Dihydromyrcenol | 25.0 |
| Floralozone | 2.3 |
| Florol | 45.0 |
| Geranyl acetate | 13.0 |
| Hedione | 65.0 |
| Hexyl acetate | 10.0 |
| Cyclogalbanate | 3.0 |
| Liffarome | 13.0 |
| Linalool | 160.0 |
| Manzanate | 0.7 |
| Methyl caprate | 5.0 |
| Methyl octanoate | 5.0 |
| Galaxolide 50 IPM | 95.0 |
| Neryl acetate | 10.0 |
| Styralyl acetate | 20.0 |
| α-Terpineol | 13.0 |
| Dipropylene glycol | 21.2 |
| Vertenex | 65.0 |
| Trifernal | 3.0 |
| Undecavertol | 2.7 |
| Total | 925.0 |

INDUSTRIAL APPLICABILITY

The isobutyric acid ester compound having a carbonate group at the α-position of the present invention has an excellent aroma and is expected to be used itself as a fragrance. In addition, the compound is used as a fragrance ingredient and provides a fragrance composition having excellent aroma properties. The composition is blended in various products and exhibits desired perfuming properties.

The invention claimed is:

1. A fragrance composition comprising a compound represented by Formula (1) as an active ingredient:

(1)

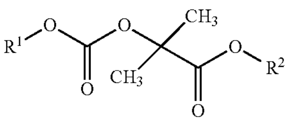

where in Formula (1), $R^1$ represents a linear, branched, or cyclic alkyl group having from 1 to 4 carbon(s); and $R^2$ represents a linear, branched, or cyclic alkyl group having from 1 to 6 carbon(s), with the proviso that the following are excluded:

a compound where $R^1$ is an n-butyl group and $R^2$ is an ethyl group; and a compound where $R^1$ is an ethyl group and $R^2$ is an ethyl group.

2. The fragrance composition according to claim 1, wherein in Formula (1), $R^1$ is a methyl group or an ethyl group.

3. The fragrance composition according to claim 1, wherein in Formula (1), $R^2$ is an isopropyl group, a sec-butyl group, or an isobutyl group.

4. A compound represented by Formula (2):

(2)

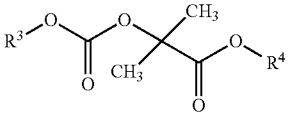

where in Formula (2), $R^3$ represents a linear, branched, or cyclic alkyl group having from 1 to 4 carbon(s); and $R^4$ represents a linear, branched, or cyclic alkyl group having from 1 to 6 carbon(s), with the proviso that the following are excluded:

a compound where $R^3$ is an ethyl group and $R^4$ is a methyl group;

a compound where $R^3$ is an ethyl group and $R^4$ is an ethyl group; and a compound where $R^3$ is a n-butyl group and $R^4$ is an ethyl group.

5. The compound according to claim 4, wherein in Formula (2), $R^3$ is a methyl group or an ethyl group.

6. The compound according to claim 4, wherein in Formula (2), $R^4$ is an isopropyl group, a sec-butyl group, or an isobutyl group.

* * * * *